United States Patent [19]

Shum et al.

[11] Patent Number: 4,935,101

[45] Date of Patent: Jun. 19, 1990

[54] PROCESS FOR THE RECOVERY OF A WATER-INSOLUBLE EPOXY ALCOHOL

[75] Inventors: Wilfred P. Shum, West Chester; Christopher J. Sowa, Media, both of Pa.

[73] Assignee: Arco Chemical Technology, Inc., Wilmington, Del.

[21] Appl. No.: 420,859

[22] Filed: Oct. 13, 1989

[51] Int. Cl.$^5$ .................. B01D 3/10; C07D 301/32
[52] U.S. Cl. .................. 203/48; 159/DIG. 16; 159/DIG. 23; 203/67; 203/69; 203/70; 203/77; 203/80; 549/529; 549/541; 549/542; 549/554
[58] Field of Search .................. 203/48, 67, 69, 70, 203/77, 80, 68, 76, 79; 159/DIG. 16, DIG. 23, 38; 549/529, 541, 542, 554

[56] References Cited

U.S. PATENT DOCUMENTS

| | | | |
|---|---|---|---|
| 2,838,524 | 6/1958 | Wilson | 549/554 |
| 3,374,153 | 3/1968 | Naglieri | 549/529 |
| 3,452,055 | 6/1969 | Golden et al. | 549/529 |
| 3,509,183 | 4/1970 | Wenzke et al. | 549/541 |
| 3,655,524 | 4/1972 | Mednick | 549/541 |
| 3,849,451 | 11/1974 | Stein et al. | 549/541 |
| 3,920,708 | 11/1975 | Kubo et al. | 549/541 |
| 3,954,815 | 4/1976 | Fisher et al. | 549/541 |
| 4,381,222 | 4/1983 | Brossmann et al. | 203/95 |
| 4,471,130 | 9/1984 | Katsuki et al. | 549/523 |
| 4,594,439 | 6/1986 | Katsuki et al. | 549/523 |

FOREIGN PATENT DOCUMENTS

| | | | |
|---|---|---|---|
| 197766 | 10/1986 | European Pat. Off. | |
| 0167579 | 9/1984 | Japan | 549/541 |
| 0189817 | 12/1966 | U.S.S.R. | 549/541 |
| 0480695 | 8/1975 | U.S.S.R. | 549/529 |
| 1023446 | 3/1966 | United Kingdom | 549/529 |
| 1072698 | 6/1967 | United Kingdom | 549/542 |

OTHER PUBLICATIONS

Sharpless [J. Am. Chem. Soc., 109, 5765, (1987)].

*Primary Examiner*—Virginia Manhoran
*Attorney, Agent, or Firm*—Stephen D. Harper

[57] ABSTRACT

Water-insoluble crystallizable epoxy alcohols such as phenyl glycidol are recovered from epoxidation reaction mixtures by washing the mixture with water, concentrating the mixture by distillation under vacuum to remove unreacted hydroperoxide and alcohol co-product, and crystallizing the epoxy alcohol from solution. Minimal decomposition of the epoxy alcohol is observed.

27 Claims, No Drawings

PROCESS FOR THE RECOVERY OF A WATER-INSOLUBLE EPOXY ALCOHOL

FIELD OF THE INVENTION

This invention pertains to methods for the recovery of a water-insoluble crystalline epoxy alcohol such as phenyl glycidol from an epoxidation reaction mixture.

BACKGROUND OF THE INVENTION

The transition metal catalyzed epoxidation of ethylenically unsaturated substrates using organic hydroperoxides as oxidants is a well known method for the preparation of epoxides. In one variation of this technology, optically active epoxy alcohols are prepared by reacting allylic alcohols with organic hydroperoxides in the presence of transition metal catalysts containing chiral ligands. The optically active epoxy alcohol products are of great value as intermediates in the synthesis of compounds having high physiological activity.

However, the recovery of epoxy alcohols from crude epoxidation reaction mixtures is complicated by the numerous components typically present in such mixtures. The reaction mixture will normally contain the epoxy alcohol, unreacted organic hydroperoxide (usually used in excess), unreacted allylic alcohol, transition metal catalyst, the organic alcohol coproduct derived from the reacted hydroperoxide, and solvent. Epoxy alcohols tend to be highly reactive and susceptible to decomposition at elevated temperatures, particularly in the presence of Lewis acids such as the transition metal compounds typically used as catalysts in epoxidation reactions.

Methods have been developed for the recovery of water-soluble non-crystalline epoxy alcohols such as glycidol. Such methods are described, for example, in U.S. Pat. No. 3,374,153 and USSR Inventor's Certificate No. 480,695. However, these methods are generally not suitable for the recovery of water-insoluble crystalline epoxy alcohols since they rely on either extracting the epoxy alcohol into an aqueous phase or distillation of the epoxy alcohol. Water-insoluble epoxy alcohols tend to be significantly higher in molecular weight and lower in volatility than the water-soluble epoxy alcohols and thus cannot be readily distilled without significant decomposition taking place.

Sharpless [*J. Am. Chem. Soc.* 109, 5765(1987)] teaches the purification of water-insoluble crystalline epoxy alcohols by various multi-step procedures. These procedures are not readily adaptable to commercial epoxy alcohol production due to either inherent safety hazards, the use of large quantities of materials such as magnesium sulfate and diatomaceous earth, or the tedious nature of the several steps required.

Clearly, there is a need for a practical, economical method whereby a water-insoluble crystalline epoxy alcohol may be separated from an epoxidation reaction mixture.

SUMMARY OF THE INVENTION

This invention provides a method for recovering a water-insoluble crystallizable epoxy alcohol from an epoxidation reaction mixture produced by contacting an allylic alcohol with an aliphatic hydroperoxide in a first organic solvent selected from the group consisting of halogenated aliphatic hydrocarbons, aliphatic hydrocarbons, and mixtures thereof in the presence of a transition metal catalyst wherein the organic solvent is from 75 to 95 weight percent of the epoxidation reaction mixture. The epoxidation reaction mixture will generally contain the epoxy alcohol, the aliphatic alcohol derived from the aliphatic hydroperoxide, unreacted allylic alcohol, excess aliphatic hydroperoxide, catalyst, and the organic solvent.

In the first step of this method, the epoxidation reaction mixture is washed with a volume of water effective to remove at least a portion of the aliphatic alcohol and unreacted aliphatic hydroperoxide. At least about 50 percent of the organic solvent is then removed from the washed reaction mixture by distilling under vacuum at a temperature sufficient to maintain homogeneity without causing significant decomposition of the epoxy alcohol. A second organic solvent is then added to the stripped solution to form a diluted solution wherein the weight of the second aromatic solvent is at least equivalent to the initial weight of the mixture. The second organic solvent is selected from the group consisting of aliphatic hydrocarbons and aromatic hydrocarbons. Substantially all of the remaining aliphatic alcohol and unreacted aliphatic hydroperoxide is removed by distilling the diluted solution under vacuum at a temperature sufficient to maintain homogeneity without causing significant decomposition or distillation of the epoxy alcohol. Sufficient organic solvent is also removed to give a concentrated solution containing from about 50 to 75 weight percent total organic solvent. The concentrated solution is cooled to a temperature sufficient to crystallize the epoxy alcohol, which is then separated from the remainder of the concentrated solution.

This invention also provides a method for recovering a water-insoluble crystallizable epoxy alcohol from an epoxidation reaction mixture containing an organic solvent selected from the group consisting of aliphatic hydrocarbons, aromatic hydrocarbons, and mixtures thereof. The epoxidation reaction mixture is washed with a volume of water sufficient to remove at least a portion of the aliphatic alcohol and unreacted aliphatic hydroperoxide present in the reaction mixture. Substantially all of the remaining aliphatic alcohol and unreacted aliphatic hydroperoxide is then removed by distilling the washed mixture under vacuum at a temperature sufficient to maintain homogeneity without causing significant decomposition or distillation of the epoxy alcohol. Sufficient organic solvent is also removed to give a concentrated solution containing from about 50 to 75 weight percent of organic solvent. The concentrated solution is cooled to a temperature sufficient to crystallize the epoxy alcohol, which may then be separated from the remainder of the concentrated solution.

DETAILED DESCRIPTION OF THE INVENTION

Epoxy alcohols suitable for purification by the process of this invention include those organic compounds having at least one epoxy and at least one alcohol functionality which are substantially water-insoluble and crystallizable. Preferably, the water-solubility of the epoxy alcohol is less than about 50 g per liter; more preferably, it is less than about 10 g per liter. The crystalline melting point of the epoxy alcohol is preferably at least about 25° C. Recovery is generally more complete, however, if the crystalline melting point is at least about 40° C.

The epoxy alcohol may contain any type of substituent, provided the substituents do not render the epoxy alcohol water-soluble or non-crystallizable. The process of this invention is particularly well-suited for the recovery of aromatic epoxy alcohols such as phenyl glycidol. Racemic, achiral, or chiral epoxy alcohols can be purified using the instant invention. In recovering an epoxy alcohol from an asymmetric epoxidation mixture, the use of the process of this invention often results in an enhancement of the optical purity compared to products recovered by other methods.

Suitable epoxy alcohols which may be purified by the process of this invention include, but are not limited to, compounds having the general structure

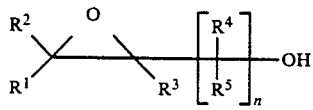

where in $n=1-3$ and $R^1, R^2, R^3, R^4$, and $R^5$ are the same or different and are radicals selected from the group consisting of hydrogen, $C_1$–$C_{12}$ linear or branched saturated or unsaturated alkyl, cycloalkyl, aralkyl, aryl, substituted aryl, halo alkyl, alkoxyalkyl, aryloxyalkyl, and aralkoxyalkyl. To be water-insoluble and crystallizable, at least one of $R^1, R^2, R^3, R^4$, and $R^5$ must be a radical other than hydrogen and preferably is an aryl, aralkyl, substituted aryl, aryloxyalkyl, or aralkoxyalkyl radical or an alkyl, halo alkyl, cycloalkyl, or halo alkyl radical containing at least 5 carbon atoms.

More preferably, the epoxy alcohol has the following general structure

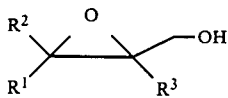

wherein one of $R^1, R^2$, or $R^3$ is phenyl or substituted phenyl and the remaining R groups are hydrogen.

Illustrative water-insoluble crystallizable epoxy alcohols include phenyl glycidol (3-phenyl-oxirane methanol), 3-(4-nitrophenyl)oxirane methanol, 3-(4-bromophenyl) oxirane methanol, 3-heptyloxirane methanol, 3-octyl oxirane methanol, 3-(benzyloxymethyl)oxirane methanol, 2-tetradecyloxirane methanol, 2-methyl-3-phenyloxirane methanol, 2-phenyloxirane methanol, 2,3-diphenyloxirane methanol, 3-naphthyloxirane methanol, 2-cyclohexyloxirane methanol, 1-phenyloxirane methanol, 3-phenyloxirane ethanol, and 2-(4-methyl)oxirane methanol.

Methods of producing epoxidation reaction mixtures suitable for purification by the process of this invention are well-known in the art. Such methods generally involve the reaction of an aliphatic hydroperoxide with an allylic alcohol in the presence of a transition metal catalyst and an organic solvent as described, for example, in R. A. Sheldon *Aspects Homogeneous Catal.* 4, 3(1981) and K. A. Jorgensen *Chem. Rev.* 89, 431(1989). The teachings of these papers are incorporated herein by reference in their entirety. The aliphatic hydroperoxide is preferably tertiary butyl hydroperoxide, due to its low cost and stability, but other water-soluble aliphatic hydroperoxides such as tertiary amyl hydroperoxide may also be used. The transition metal catalyst is preferably selected from the group consisting of compounds of titanium, molybdenum, zirconium, vanadium, tantalum, and tungsten.

The process of this invention is particularly useful for the recovery of chiral, water-insoluble, crystallizable epoxy alcohols from epoxidation reaction mixtures. The asymmetric epoxidation of allylic alcohols using organic hydroperoxides and chiral transition metal complex catalysts such as titanium tetraalkoxide/chiral tartrate catalysts is described in the following references: U.S. Pat. Nos. 4,471,130 and 4,764,628; European Pat. Nos. 197,766, 70,618, and 255,379; A. Pfenninger *Synthesis* 89(1986); Y. Gao et al *J. Am. Chem. Soc.* 109,5765(1987); T. Katsuki et al *J. Am. Chem. Soc.* 102, 5974(1980); M. G. Finn et al in Asymmetric Synthesis Morrison, J D., Ed., Academic Press, New York (1985), Vol. 5, Chapter 8, 247; B. E. Rossiter in *Asymmetric Synthesis* Morrison, J. D., Ed., Academic Press, New York (1985), Vol. 5, Chapter 7, 193. The teachings of these patents and papers are incorporated herein by reference.

The epoxidation reaction may be carried out in an organic solvent selected from the group consisting of aromatic hydrocarbons, aliphatic hydrocarbons, and halogenated aliphatic hydrocarbons. The organic solvent should be a liquid at the epoxidation reaction temperature and should be miscible with or capable of dissolving the epoxidation reactants and products (i.e., the aliphatic hydroperoxide, allylic alcohol, epoxy alcohol, the aliphatic alcohol derived from the aliphatic hydroperoxide, and so forth). Preferably, the boiling point of the organic solvent is between about 25° C. and 175° C. at atmospheric pressure and the freezing point is below about −25° C. The organic solvent should be substantially inert to the reactants and products of the epoxidation reaction.

Suitable aromatic hydrocarbons include, but are not limited to, benzene, toluene, xylene (o, m, or p), cumene, ethylbenzene, chlorobenzene, mesitylene, t-butyl benzene, and the like and their mixtures.

Aliphatic hydrocarbons appropriate for use as the organic solvent in the process of this invention include $C_5$ to $C_{10}$ linear, branched, and cyclic aliphatic hydrocarbons and their mixtures. Illustrative aliphatic hydrocarbons include pentane, hexane, heptane, octane, nonane, decane, 2-methylbutane (isopentane), 2,2,4-trimethyl pentane(isooctane), cyclohexane, methyl cyclohexane, 2-methyl pentane(isohexane), 2,2-dimethylhexane, 2,5-dimethylhexane, 2-methylheptane, 4-methylheptane, and the like. Mixtures of aliphatic hydrocarbons such as petroleum ether, hexanes, naphtha, ligroin and benzin may be used.

Halogenated aliphatic hydrocarbons useful as the organic solvent in this invention include, but are not limited to, methylene chloride, dichloroethane, chloroform, carbon tetrachloride, trichloroethane, tetrachloroethane, chloropropane, dichloropropane, trichloropropane, and the like and mixtures thereof. Mixtures of halogenated aliphatic hydrocarbons, aromatic hydrocarbons, and aliphatic hydrocarbons may also be employed in this process.

If the epoxidation reaction mixture contains a heterogeneous transition metal catalyst or molecular sieves (as described in European Pat. No. 197,766, for example) it is generally desirable to first filter the mixture to remove this insoluble material before the washing step.

In the washing step, the epoxidation reaction mixture is contacted with a volume of water sufficient to remove at least a portion of the aliphatic alcohol and unreacted aliphatic hydroperoxide. In general, it is preferred that the volume of water used is from about 0.05 to 2 times the volume of the epoxidation reaction mixture. Preferably, the washing step removes at least about 25 percent each of the aliphatic alcohol and hydroperoxide. The water wash also serves to at least partially remove any water-soluble acidic impurities present in the mixture. These impurities, if not removed, may promote decomposition of the epoxy alcohol product during the later stages of the recovery process. For this reason, it is preferable that the water contain a base dissolved therein in order to neutralize any acidic species present. The base may be an alkali metal hydroxide, carbonate, or bicarbonate, for example, and is preferably present in the water at concentrations of from about 0.1 to 5 weight percent.

The washing step may be performed using any liquid-liquid extraction method known in the art. For example, the water may simply be mixed with the reaction mixture with agitation and the phases allowed to separate. This may be repeated several times with fresh portions of water. Counter-current extraction may also be used in which the water and the reaction mixture are caused to flow past or through one another in opposite directions in a vertical tube or tower. The temperature of the water wash step is not critical, although it should be sufficiently high to maintain homogeneity of the reaction mixture but not so high as to result in decomposition of the epoxy alcohol. For convenience, wash temperatures between about 10° C. and 75° C. are generally appropriate.

If the organic solvent present in the epoxidation reaction mixture is an aromatic hydrocarbon or aliphatic hydrocarbon and this solvent is suitable for use in the crystallization step of this process, the next step will be to strip the washed reaction mixture by distillation under vacuum in order to remove substantially all of the remaining aliphatic hydroperoxide and aliphatic alcohol. In general, it is preferred that about 90 percent of the amount of these components present in the initial epoxidation reaction mixture be removed. At the same time, sufficient organic solvent is removed to give a concentrated solution containing from about 50 to 75 weight percent organic solvent. The exact temperature and vacuum employed are not critical and will, of course, vary depending on the boiling points of the solvent, alcohol, and hydroperoxide but are adjusted so that homogeneity of the concentrated solution is maintained and loss of the desired epoxy alcohol product by decomposition or overhead distillation is minimized. Generally speaking, pot temperatures of from about 0° C. to 100° C. and pressures of from about 0.1 to 350 mm Hg are suitable. More preferably, the distillation is carried out at a temperature of between about 20° C. and 75° C. and a pressure of from about 1.0 to 200 mm.

Without wishing to be bound by theory, it is believed that the presence of the organic solvent during the concentration step helps to lower the effective boiling point of the aliphatic hydroperoxide and alcohol. The removal of these components from the reaction mixture is thus facilitated by the organic solvent. Without the organic solvent, higher pot temperatures would be necessary, resulting in more substantial decomposition of the epoxy alcohol. It has been found that recovery of the epoxy alcohol by crystallization is difficult unless the alcohol and hydroperoxide are first removed.

The concentrated solution is then cooled to a temperature sufficient to crystallize at least a portion of the epoxy alcohol. The exact temperature is not critical, although it should be above the freezing point of the organic solvent. Preferably, at least about 25% of the epoxy alcohol in the concentrated solution is crystallized. More preferably, at least about 40% is crystallized. Temperatures between about −30° C. and 30° C. are generally suitable, but the temperature may be varied as may be desired depending on the concentration and solubility of the epoxy alcohol in the concentrated solution. Seed crystals of crystalline epoxy alcohol may be added to the concentrated solution to hasten the crystallization process.

The crystallized epoxy alcohol is then separated from the remainder of the concentrated solution by any appropriate method. Filtration, decantation, and centrifugation are examples of separation methods which can be employed for this purpose. The separated epoxy alcohol may be washed with additional organic solvent to remove any impurities on the surface of the crystals. The organic solvent may be the same as or different from the solvent used in the crystallization, but it should be one in which the epoxy alcohol has limited solubility. For example, if a high boiling solvent is employed as the crystallization solvent, the washing solvent can be a low boiling solvent so that the epoxy alcohol may be more readily dried. Drying may be accomplished by any convenient method, but preferably is carried out at a temperature at least about 10° C. below the melting point of the epoxy alcohol.

Additional epoxy alcohol can generally be recovered by concentrating the filtrate using distillation procedures similar to those described previously and then cooling the concentrated solution to cause the epoxy alcohol to crystallize from solution.

Alternatively, if the organic solvent in the epoxidation reaction mixture is a halogenated aliphatic hydrocarbon or if it is desired to use a different aromatic solvent or aliphatic hydrocarbon in the crystallization step of this process, the first organic solvent may be partially or fully replaced with a second organic solvent after the water-wash step by the following procedure. The water-washed reaction mixture is subjected to distillation under vacuum to remove at least about 50 percent (more preferably, at least about 75 percent) of the first organic solvent. The second organic solvent, the weight of which is at least equivalent to the weight of the stripped mixture, is then added to form a diluted solution. Additional organic solvent is then removed by distillation under vacuum until a concentrated solution containing from about 50 to 75 weight percent total organic solvent is obtained. By the end of this distillation step, substantially all of the remaining aliphatic hydroperoxide and alcohol has been removed. The concentrated solution may then be cooled to crystallize the epoxy alcohol as described above. In both of the stripping/distillation steps of this embodiment of the process, the temperature of the mixture is sufficiently high that homogeneity is maintained but not so high as to cause significant loss of the epoxy alcohol either by distillation or decomposition. Although the optimum conditions will be determined by the particular solvents, reactants, and products involved, pot temperatures of from about 0° C. to 100° C. (more preferably, about 20° C. to 75° C.) and pressures of from about 0.1 to 350 mm Hg are generally preferred.

In a particularly preferred embodiment of this process, the first organic solvent is a halogenated aliphatic hydrocarbon such as methylene chloride and the second organic solvent is an aromatic hydrocarbon such as toluene. However, from the foregoing description one skilled in the art can readily ascertain the essential characteristics of this invention and, without departing from the spirit and scope thereof, can make various changes and modifications of the invention to adopt it to various usages, conditions, and embodiments.

The following examples further illustrate this invention, but are not limitative of the invention in any manner whatsoever.

EXAMPLE 1

This example illustrates the recovery of phenyl glycidol from an epoxidation reaction mixture using the process of this invention.

A. Preparation of Anhydrous Hydroperoxide Solution

A 114 kg portion of 70% tertiary butyl hydroperoxide in water was batch extracted into 2,2,4-trimethyl pentane. The aqueous layer was drawn off and discarded after phase separation. Residual water in the organic phase was removed by azeotropic distillation (40° C.; 100 mm Hg), with the distilled 2,2,4-trimethyl pentane recycled to the tertiary butyl hydroperoxide solution after separation from the water. The anhydrous TBHP solution obtained weighed 242 kg and contained 28 weight percent TBHP and 0.4 weight percent water.

B. Asymmetric Epoxidation of Cinnamyl Alcohol

A 300 gallon glass lined reactor vessel was charged with 50 kg cinnamyl alcohol, 6 kg D(-)-diisopropyltartrate, 1000 kg methylene chloride, and 20 kg 4 Å molecular sieves. After cooling the reaction mixture to −10° C., titanium isopropoxide (5.3 kg) and then the anhydrous TBHP solution (242 kg) were added with agitation. The contents of the reactor were maintained at a temperature of between −10 to −20° C. with continuous agitation for about 8 hours. A cinnamyl alcohol conversion of at least about 80 percent was achieved, as determined by capillary GC and TLC analysis. The crude epoxidation reaction mixture contained approximately 3.1 weight percent unreacted TBHP, 0.8 weight percent unreacted cinnamyl alcohol, 3.4 weight percent phenyl glycidol, and 1.7 weight percent tertiary butyl alcohol.

C. Phenyl Glycidol Recovery

The molecular sieves were removed by filtration before water extracting the reaction mixture in a reciprocating plate Karr column using a water/feed ratio of 0.3/1 v/v. The water wash removed approximately 51 percent of the TBHP and 32 percent of the tertiary butyl alcohol.

The washed reaction mixture was then stripped under vacuum to remove essentially all of the 2,2,4-trimethyl pentane and methylene chloride using a wiped film evaporator and a flash temperature of no higher than 50° C. The stripped reaction mixture (approximately 101 kg in weight) was blended with 170 kg toluene and reconcentrated by heating under vacuum (20°–50° C.; 20 mm Hg) to remove essentially all of the remaining TBHP and tertiary butyl hydroperoxide and approximately half of the toluene. The concentrated solution, which contained about 30 weight percent phenyl glycidol and 56 weight percent toluene, was cooled to about 0° C. to precipitate crystalline phenyl glycidol. The crystalline product was collected by filtration and washed with cold toluene/hexane and then cold hexanes to yield 29 kg (52% overall yield; 65% recovery) of colorless (R)-phenyl glycidol having a melting point of 51°–52° C. (lit. 51.5°–53° C.). The enantiomeric excess (e.e.) was >95%, as determined by the $^{13}C$ NMR Mosher ester method [Dale et al *J. Org. Chem.* 34, 2543(1969); Gao et al *J. Am. Chem. Soc.* 109, 5765(1987)].

EXAMPLE 2

This example demonstrates the recovery of an alkyl substituted epoxy alcohol from an epoxidation reaction mixture using a single solvent throughout the entire process.

A mixture of 400 g 2,2,4-trimethylpentane, 50 g (0.48 moles) t-amyl hydroperoxide, 42.95 g (0.27 moles) (Z)-2-decen-1-ol, and 0.10 g vanadyl acetylacetonate is heated at 80° C with agitation in a 1 L round bottom flask for 45 minutes under a nitrogen atmosphere. After cooling to about 25° C, the mixture is extracted with 50 mL portions of 1% aqueous sodium carbonate in a separatory funnel until at least about 25 percent each of the unreacted t-amyl hydroperoxide and the t-amyl alcohol are removed.

Substantially all of the remaining hydroperoxide and alcohol are then removed by distillation under vacuum (40°–60° C.; 100 mm Hg). Sufficient 2,2,4-trimethylpentane is also removed (about 25%) to give a concentrated solution containing about 60% solvent. The concentrated solution is cooled 18 hours at −20° C. to give crystalline cis-3-heptyl oxirane methanol, which is collected by filtration and washed with three 25 mL portions of cold petroleum ether (b.p. 30°–60°).

EXAMPLE 3

A mixture of 450 g dichloroethane, 35.8 g (0.20 mole) (E)-3-(4-nitrophenyl)-2-propenol, 27.0 g (0.30 mole) t-butyl hydroperoxide, and 0.05 g molybdenum hexacarbonyl is heated at 60° C. with agitation in a 1 L round bottom flask for 2 hours under a nitrogen atmosphere. After cooling to about 25° C., the mixture is washed with 50 mL portions of water in a separatory funnel until at least about 50 percent each of the unreacted tertiary butyl hydroperoxide and tertiary butyl alcohol are removed.

Approximately 300 g of the washed organic layer is then removed by distillation under vacuum (40°–60° C.; to give a concentrated solution containing about 30 weight percent dichloroethane. The solution is diluted with 300 g m-xylene and then distilled under vacuum (40°–60° C.) to remove substantially all of the remaining t-butyl alcohol and t-butylhydroperoxide and to give a final solvent concentration of about 70 weight percent. Crystalline (trans)-3-(4-nitrophenyl) oxirane methanol is obtained by cooling the mixture at 0° C. for 24 hours, filtering, washing with two 25 mL volumes of cold hexanes, and drying 12 hours at 25° C. under vacuum (100 mm).

We claim:

1. A method of recovering a water-insoluble crystallizable epoxy alcohol from an epoxidation reaction mixture, said method comprising:

(a) washing the epoxidation reaction mixture, which contains an aliphatic alcohol and is produced by contacting an allylic alcohol with an aliphatic hydroperoxide in a first organic solvent selected from the group consisting of halogenated aliphatic hydrocarbons, aliphatic hydrocarbons, and mixtures thereof in the presence of a transition metal catalyst and wherein the first organic solvent is from about 75 to 95 weight percent of the epoxidation reaction mixture, with a volume of water effective to remove at least a portion of the aliphatic alcohol and unreacted aliphatic hydroperoxide;

(b) forming a stripped solution by removing at least about 50 percent of the first organic solvent from the washed reaction mixture of step (a) by distilling under vacuum at a temperature sufficient to maintain homogeneity without causing significant decomposition of the epoxy alcohol;

(c) adding a second organic solvent selected from the group consisting of aliphatic hydrocarbons and aromatic hydrocarbons to the stripped solution to form a diluted solution, wherein the weight of the second organic solvent is at least equivalent to the weight of the stripped solution;

(d) removing substantially all of the remaining aliphatic alcohol and unreacted aliphatic hydroperoxide and sufficient organic solvent to form a concentrated solution containing from about 50 to 75 weight percent total organic solvent by distilling the diluted solution under vacuum at a temperature sufficient to maintain homogeneity without causing significant decomposition of the epoxy alcohol;

(e) cooling the concentrated solution to a temperature sufficient to crystallize at least about 25% of the epoxy alcohol; and (f) separating the crystallized epoxy alcohol.

2. The method of claim 1 wherein the epoxy alcohol is an aromatic epoxy alcohol.

3. The method of claim 1 wherein the aliphatic hydroperoxide is tertiary butyl hydroperoxide.

4. The method of claim 1 wherein the transition metal catalyst is a titanium alkoxide catalyst.

5. The method of claim 1 wherein the first organic solvent is a halogenated aliphatic hydrocarbon selected from the group consisting of methylene chloride, dichloroethane, chloroform, carbon tetrachloride, dichloropropane, trichloropropane, trichloroethane, chloropropane, tetrachloroethane, and mixtures thereof.

6. The method of claim 1 wherein the first or second organic solvent is an aliphatic hydrocarbon selected from the group consisting of $C_5$ to $C_{10}$ linear, branched, and cyclic aliphatic hydrocarbons and mixtures thereof.

7. The method of claim 1 wherein the second organic solvent is an aromatic hydrocarbon selected from the group consisting of benzene, toluene, xylene, ethylbenzene, cumene, and mixtures thereof.

8. The method of claim 1 wherein the water contains a base dissolved therein.

9. A method of recovering a water-insoluble crystallizable aromatic epoxy alcohol from an epoxidation reaction mixture, said method comprising:

(a) washing the epoxidation reaction mixture, which contains tertiary butyl alcohol and is produced by contacting an aromatic allylic alcohol with tertiary butyl hydroperoxide in a first organic solvent selected from the group consisting of halogenated aliphatic hydrocarbons, aliphatic hydrocarbons and mixtures thereof in the presence of a titanium alkoxide catalyst and wherein the first organic solvent is from about 75 to 95 weight percent of the epoxidation reaction mixture, with a volume of water effective to remove at least about 25 percent each of the tertiary butyl alcohol and unreacted tertiary butyl hydroperoxide;

(b) forming a stripped solution by removing at least about 75 percent of the first organic solvent from the washed reaction mixture of step (a) by distilling under vacuum at a temperature sufficient to maintain homogeneity without causing substantial decomposition of the aromatic epoxy alcohol;

(c) adding a second organic solvent selected from the group consisting of aliphatic hydrocarbons and aromatic hydrocarbons to the stripped solution to form a diluted solution wherein the weight of the aromatic solvent is at least equivalent to the weight of the stripped solution;

(d) removing substantially all of the remaining tertiary butyl alcohol and unreacted tertiary butyl hydroperoxide and sufficient organic solvent to give a concentrated solution containing from about 50 to 75 weight percent total of organic solvent by distilling the diluted solution under vacuum at a temperature sufficient to maintain homogeneity without causing significant decomposition of the aromatic epoxy alcohol;

(e) cooling the concentrated solution to a temperature sufficient to crystallize at least about 25% of the aromatic epoxy alcohol; and (f) separating the crystallized aromatic epoxy alcohol.

10. The method of claim 9 wherein the aromatic epoxy alcohol is phenyl glycidol.

11. The method of claim 9 wherein the titanium alkoxide catalyst is a titanium tetraalkoxide and chiral tartrate complex catalyst.

12. The method of claim 9 wherein the first organic solvent is a halogenated aliphatic hydrocarbon selected from the group consisting of methylene chloride, dichloroethane, chloroform, carbon tetrachloride, trichloroethane, chloropropane, tetrachloroethane and mixtures thereof.

13. The method of claim 9 wherein the first or second organic solvent is an aliphatic hydrocarbon selected from the group consisting of $C_5$ to $C_{10}$ linear and branched aliphatic hydrocarbons and mixtures thereof.

14. The method of claim 9 wherein the first or second organic solvent is selected from the group consisting of benzene, toluene, xylene, ethyl benzene, cumene, and mixtures thereof.

15. The method of claim 9 wherein the first organic solvent is methylene chloride and the second organic solvent is toluene.

16. The method of claim 9 wherein the water contains a base dissolved therein.

17. A method of recovering a water-insoluble crystallizable epoxy alcohol from an epoxidation reaction mixture, said method comprising:

(a) washing the epoxidation reaction mixture, which contains an aliphatic alcohol and is produced by contacting an allylic alcohol with an aliphatic hydroperoxide in an organic solvent selected from the group consisting of aliphatic hydrocarbons, aromatic hydrocarbons, and mixtures thereof in the presence of a transition metal catalyst and wherein the organic solvent is from about 75 to 95 weight percent of the epoxidation reaction mixture, with a volume of water sufficient to remove at least a portion of the aliphatic alcohol and unreacted aliphatic hydroperoxide;

(b) removing substantially all of the remaining aliphatic alcohol and unreacted aliphatic hydroperoxide and sufficient organic solvent to give a concentrated solution containing from about 50 to 75 weight percent of organic solvent by distilling the washed mixture under vacuum at a temperature sufficient to maintain homogeneity without causing significant decomposition of the epoxy alcohol;

(c) cooling the concentrated solution to a temperature sufficient to crystallize at least about 25% of the epoxy alcohol; and (d) separating the crystallized epoxy alcohol.

18. The method of claim 17 wherein the epoxy alcohol is an aromatic epoxy alcohol.

19. The method of claim 17 wherein the aliphatic hydroperoxide is tertiary butyl hydroperoxide.

20. The method of claim 17 wherein the transition metal catalyst is a titanium alkoxide catalyst.

21. The method of claim 17 wherein the organic solvent is an aliphatic hydrocarbon selected from the group consisting of $C_5$ to $C_{10}$ linear, branched, and cyclic aliphatic hydrocarbons and mixtures thereof.

22. The method of claim 17 wherein the organic solvent is an aromatic solvent selected from the group consisting of benzene, toluene, xylene, ethyl benzene, cumene, and mixtures thereof.

23. A method of recovering a water-insoluble crystallizable aromatic epoxy alcohol from a homogeneous epoxidation reaction mixture, said method comprising:

(a) washing the epoxidation reaction mixture, which contains tertiary butyl alcohol and is produced by contacting an aromatic allylic alcohol with tertiary butyl hydroperoxide in an organic solvent selected from the group consisting of aliphatic hydrocarbons, aromatic hydrocarbons, and mixtures thereof in the presence of a titanium alkoxide catalyst and wherein the organic solvent is from about 75 to 95 weight percent of the epoxidation reaction mixture, with a volume of water sufficient to remove at least about 25 percent of the tertiary butyl alcohol and the tertiary butyl hydroperoxide;

(b) removing substantially all of the remaining tertiary butyl hydroperoxide and unreacted tertiary butyl hydroperoxide and sufficient organic solvent to give a concentrated solution containing from about 50 to 75 weight percent of organic solvent by distilling the washed mixture under vacuum at a temperature sufficient to maintain homogeneity without causing significant decomposition of the aromatic epoxy alcohol;

(c) cooling the concentrated solution to a temperature sufficient to crystallize at least about 25% of the aromatic epoxy alcohol; and (d) separating the crystallized aromatic epoxy alcohol.

24. The method of claim 23 wherein the aromatic epoxy alcohol is phenyl glycidol.

25. The method of claim 23 wherein the titanium alkoxide catalyst is a titanium tetraalkoxide and chiral tartrate complex catalyst.

26. The method of claim 23 wherein the organic solvent is an aliphatic hydrocarbon selected from the group consisting of $C_5$ to $C_{10}$ linear, branched, and cyclic aliphatic hydrocarbons and mixtures thereof.

27. The method of claim 23 wherein the organic solvent is an aromatic hydrocarbon selected from the group consisting of benzene, toluene, xylene, cumene, ethyl benzene, and mixtures thereof.

* * * * *